Figure 1:
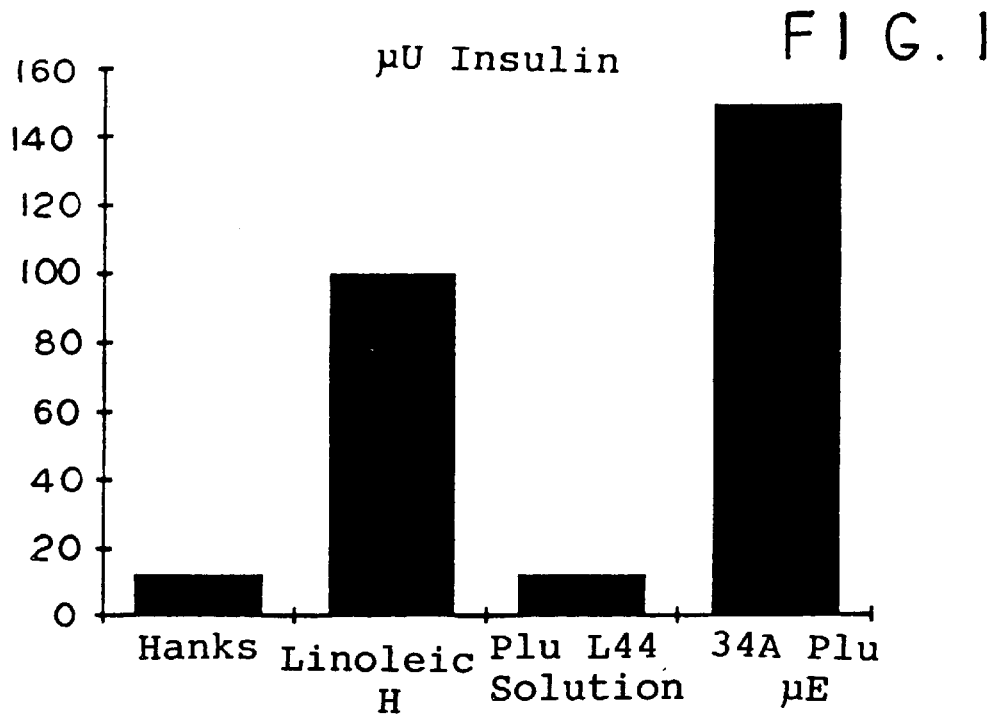

United States Patent [19]
Burnside et al.

[11] Patent Number: 5,824,638
[45] Date of Patent: Oct. 20, 1998

[54] ORAL INSULIN DELIVERY

[75] Inventors: Beth A. Burnside, Silver Spring; Carol E. Mattes, Gaithersburg; Charlotte M. McGuinness, Rockville; Edward M. Rudnic, North Potomac; George W. Belendiuk, deceased, late of Potomac, all of Md., by Krystyna Belendiuk, executrix

[73] Assignee: Shire Laboratories, Inc., Gaithersbury, Md.

[21] Appl. No.: 446,399

[22] Filed: May 22, 1995

[51] Int. Cl.$^6$ .................................................. A61K 37/26
[52] U.S. Cl. .............................................. 514/3; 530/303
[58] Field of Search ................................ 514/3; 530/303

[56] References Cited

U.S. PATENT DOCUMENTS

| | | | |
|---|---|---|---|
| 4,083,973 | 4/1978 | van der Vies | 424/238 |
| 4,115,313 | 9/1978 | Lyon et al. | 252/309 |
| 4,224,179 | 9/1980 | Schneider | 252/316 |
| 4,330,338 | 5/1982 | Banker | 106/197 |
| 4,606,913 | 8/1986 | Aronson et al. | 424/59 |
| 4,690,775 | 9/1987 | Schott et al. | 252/312 |
| 4,784,845 | 11/1988 | Desai et al. | 424/80 |
| 4,869,897 | 9/1989 | Chatterjee et al. | 424/47 |
| 4,990,337 | 2/1991 | Kurihara et al. | 424/423 |
| 5,143,934 | 9/1992 | Lading et al. | 514/386 |
| 5,206,219 | 4/1993 | Desai | 514/3 |
| 5,342,625 | 8/1994 | Hauer et al. | 424/455 |

FOREIGN PATENT DOCUMENTS

| | | |
|---|---|---|
| WO 93/02664 | 2/1993 | WIPO . |
| WO 93/02665 | 2/1993 | WIPO . |
| 9408605 | 4/1994 | WIPO . |
| WO 94/08605 | 4/1994 | WIPO . |

OTHER PUBLICATIONS

Constantinides et al., Formulation & Intestinal Absorption Enhancement Evaluation of Water–in–Oil Microemulsions Incorporating Medium–Chain Glycerides, *Pharm.Research.*, vol. 11, No. 10, pp. 1385–1390, (1994).

Ritschel et al., Improvement of Peroral Absorption of Cyclosporine A by Microemulsions, *Meth. Find.Exp. Clin, Pharmacol*, 12(2):127–134, (1990).

Shichiri et al., Increased Intestinal Absorption of Insulin in a Micellar Solution, *First Dept. of Medicine, Osaka Univ. Medical School*, pp. 175–183, (1977).

Ritschel, Microemulsions for Improved Peptide Absorption from the Gastrointestinal Tract, *Meth. Find. Exp. Clin. Pharmacol.*, 13(3): 205–220, (1991).

Kararli et al., Oral Delivery of a Renin Inhibitor Compound Using Emulsion Formulations, *Pharm.Research*, vol,9, No.7, pp. 888–893, (1992).

Myers et al., Systemic Bioavailability of Penclomedine (NSC–338720) from Oil–in–water emulsions Administered Intraduodenally to Rats, *Int'l, Jnl. of Pharmaceutics*, 78:217–226, (1992).

Bhargava et al., Using Microemulsions for Drug Delivery, *Pharm. Tech.*, pp. 47–51, (Mar. 1987).

Sarciaux et al., Using Microemulsion Formulations for Oral Drug Delivery of Therapeutic Peptides, *Intl'l. Jnl. of Pharmaceutics*, 120:127–136, (1995).

Constantinides et al., Pharmaceutical Research, 11:1385–1390, 1994.

*Primary Examiner*—Edward J. Cain
*Attorney, Agent, or Firm*—Elliot M. Olstein; Raina Semionow

[57] ABSTRACT

A pharmaceutical preparation for oral insulin delivery comprising a stable, hydrophobic emulsion comprising continuous phase of a hydrophobic material selected from the group consisting of a long chain carboxylic acid or ester or alcohol thereof dispersed in an aqueous phase or (ii) having a hydrophilic discontinuous phase dispersed in a hydrophobic phase of a long chain carboxylic acid or alcohol thereof. The emulsion with insulin is incorporated into a pharmaceutical carrier suitable for oral delivery.

18 Claims, 5 Drawing Sheets

ORAL INSULIN DELIVERY

The present invention relates to the field of pharmaceutical preparations of insulin, particularly to the field of such pharmaceutical preparations which can be administered orally.

Insulin is the mainstay for treatment of virtually all Type-I and many Type-II diabetic patients. When necessary, insulin may be administered intravenously or intramuscularly; however, long-term treatment relies on subcutaneous injection. Subcutaneous administration of insulin differs from physiological secretion of insulin in at least two major ways. First, the kinetics of absorption are relatively slow and thus do not mimic the normal rapid rise and decline of insulin secretion in response to ingestion of food, and second, the insulin diffuses into the peripheral circulation instead of being released into the portal circulation. The preferential effect of secreted insulin on the liver is thus eliminated. Nonetheless, such treatment has achieved considerable success.

Preparations of insulin can be classified according to their duration of action into short-, intermediate-, or long-acting and by their species or origin—human, porcine, bovine, or a mixture of bovine and porcine. Human insulin is now widely available as a result of its production by recombinant DNA techniques.

Attempts have been made to administer insulin orally, nasally, rectally, and by subcutaneous implantation of pellets. The most promising of these is nasal delivery. Although oral delivery of insulin would be preferred by patients and would provide higher relative concentrations of insulin in the portal circulation, attempts to increase intestinal absorption of the hormone have met with only limited success. Efforts have focused on protection of insulin by encapsulation or incorporation into liposomes. See, generally, Goodman and Gilman, the Pharmacological Bases of Therapeutics (8th Ed.), pages 1463–1495, McGraw-Hill, NY (1993).

In accordance with the present invention there is provided a pharmaceutical composition comprising insulin incorporated into a pharmaceutical carrier emulsion comprised of a hydrophobic material selected from the group consisting of a long chain carboxylic acid, long chain carboxylic acid ester, long chain carboxylic acid alcohol and mixtures thereof emulsified with a hydrophilic material.

For purposes of oral insulin delivery, the hydrophobic material forms the continuous phase and the hydrophilic material forms the discontinuous phase in which the hydrophilic material is emulsified (water-in-oil). The hydrophobic continuous phase and the hydrophilic discontinuous phase can each independently be solid, semisolid or liquid. The insulin is solvable in the hydrophilic material. Preferably the carrier emulsion is a microemulsion.

In a preferred embodiment, the invention provides a pharmaceutical preparation comprising a water-in-oil emulsion, preferably a microemulsion, containing an oil phase (such as a long chain carboxylic acid or ester or alcohol thereof), a surface active agent (such as a poloxamer) and an aqueous phase containing the insulin. The advantage of using a water-in-oil microemulsion is that it has the ability to dissolve relatively large amounts of polar solutes in an overall oily environment, creating an oral delivery system for oral delivery of active insulin.

FIG. 1 graphically illustrates the $\mu U$ insulin concentration observed to have been transported across Caco-2 cell monolayers in various preparations based on the results of the in vitro experiments described in Example 1.

Figure 2:
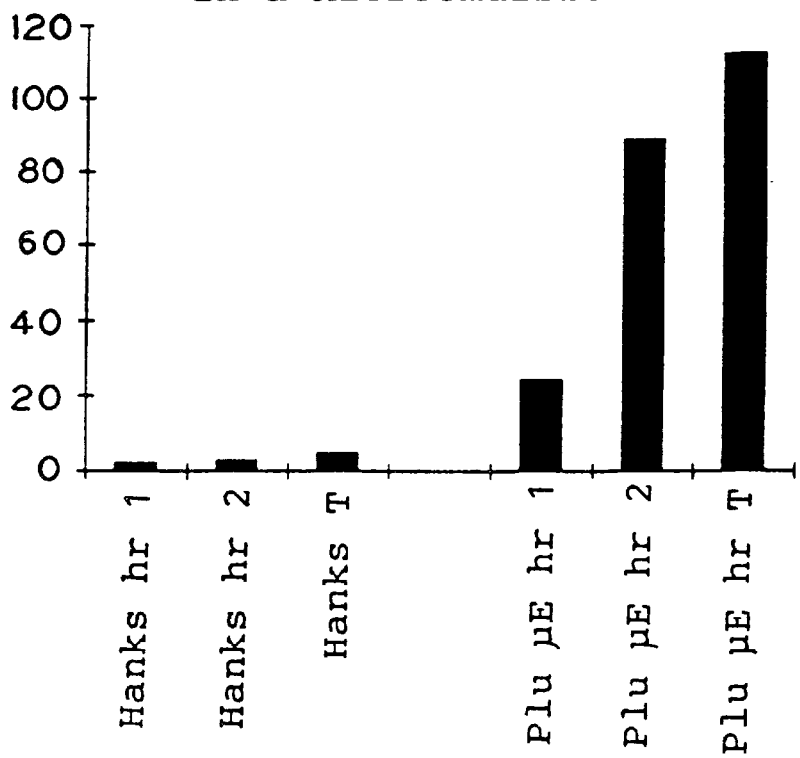

FIG. 2 graphically illustrates a comparison of insulin transport($\mu U$/mL) across Caco-2 cell monolayers in three microemulsion preparations based on the results of the in vitro experiments described in Example 1.

Figure 3:
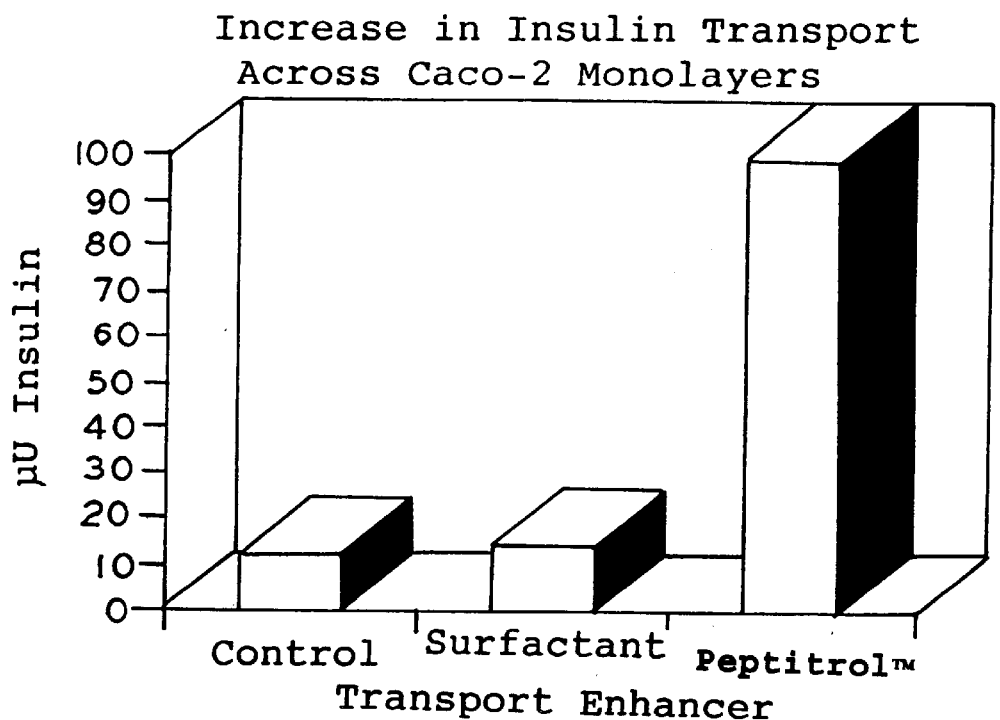

FIG. 3 graphically illustrates the increase in insulin transport across Caco-2 cell monolayers made possible by the Peptitrol™ microemulsion preparation of the invention based on the results of the in vitro experiments described in Example 1.

Figure 4:
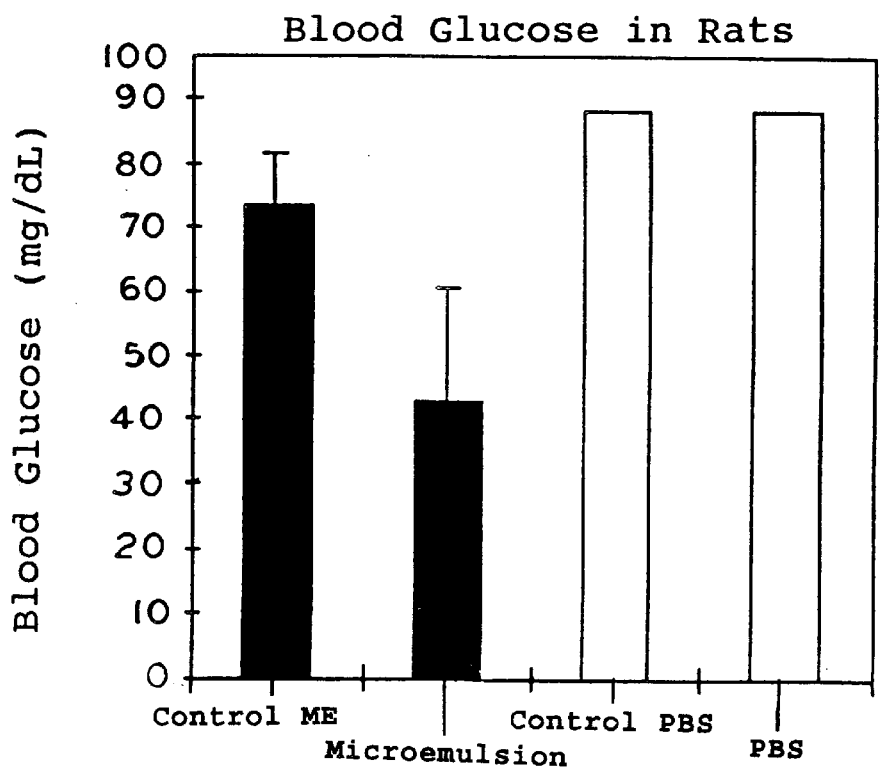

FIG. 4 graphically illustrates the control of blood glucose concentration observed in rats using various preparations based on the results of the in vivo experiments described in Example 2.

Figure 5:
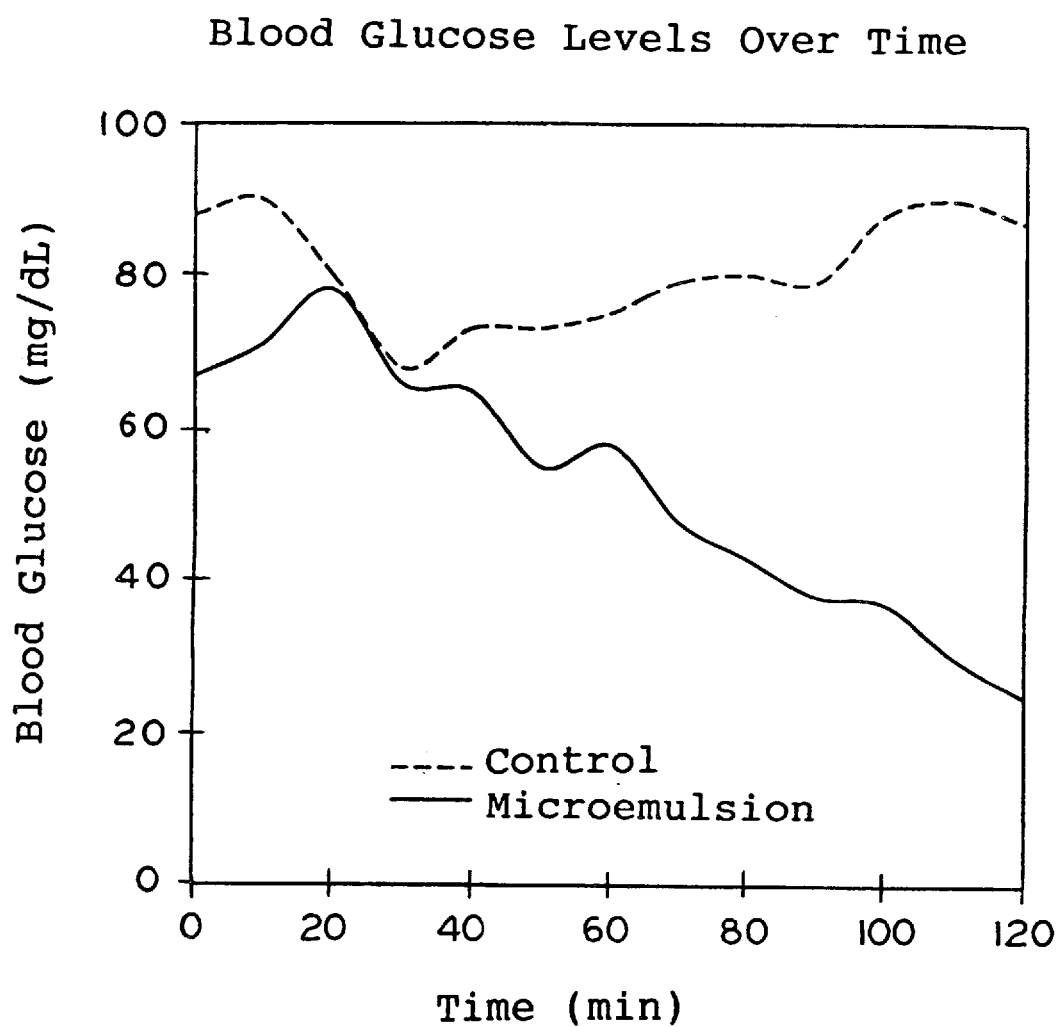

FIG. 5 graphically illustrates the control of blood glucose concentration observed in rats over two hours comparing a microemulsion preparation of the invention and a control based on the results of the in vivo experiments described in Example 2.

Figure 6:
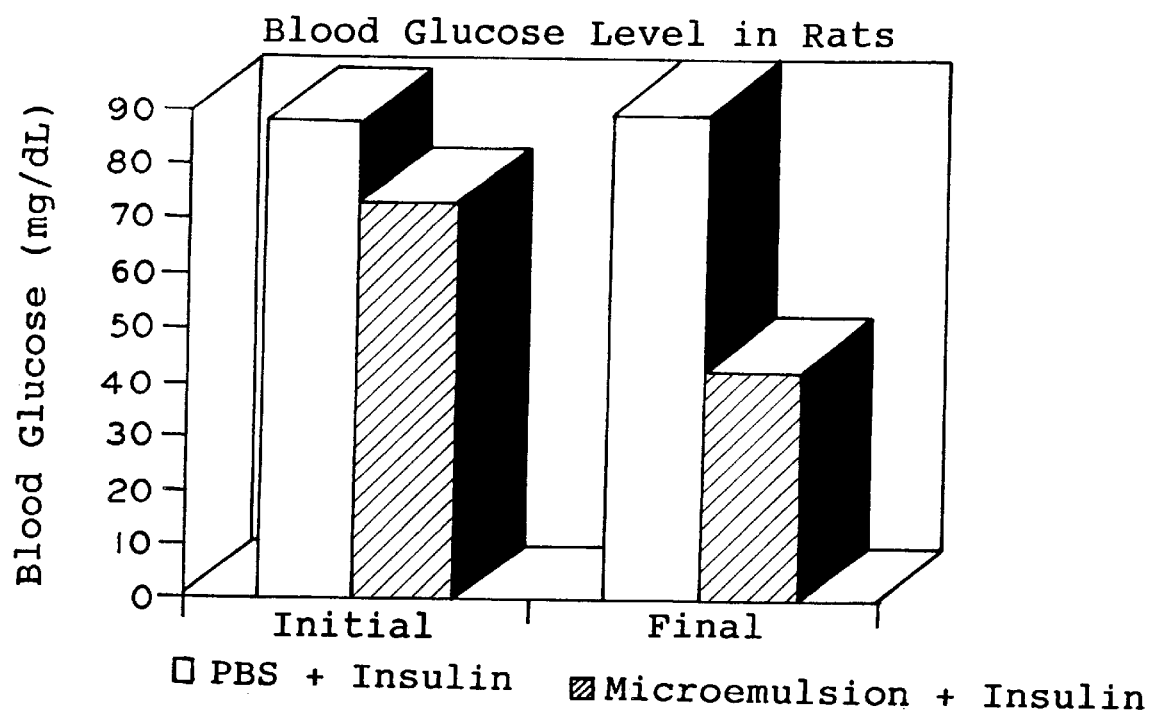

FIG. 6 graphically illustrates initial and final blood glucose concentrations observed in rats over two hours comparing a microemulsion preparation of the invention and a control based on the results of the in vivo experiments described in Example 2.

Figure 7:
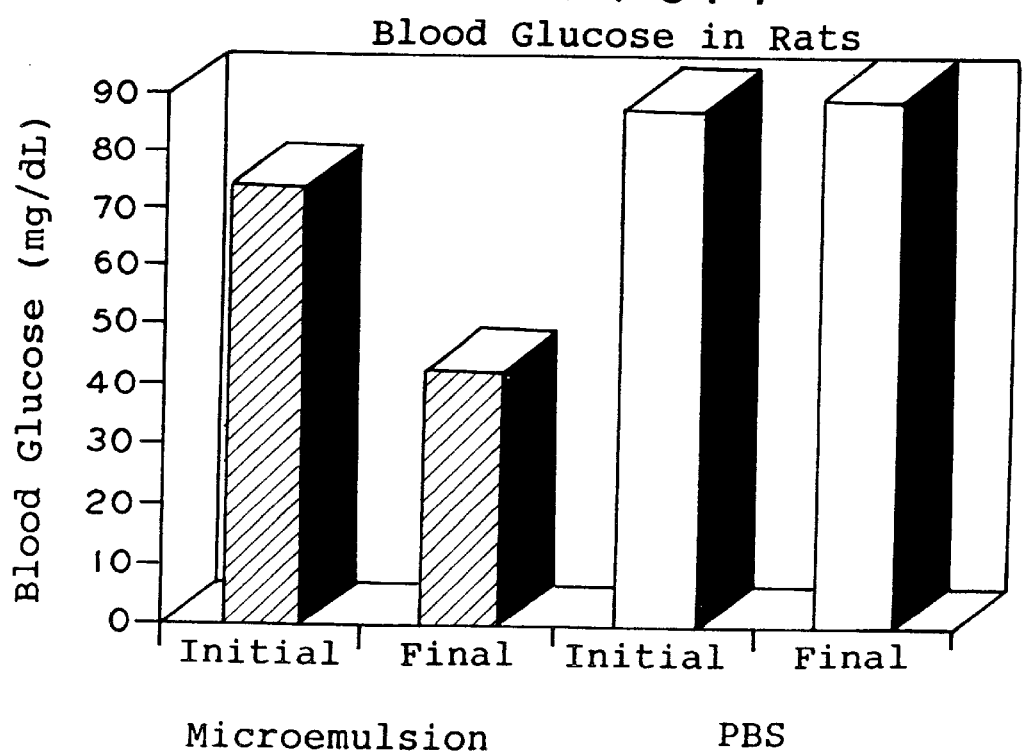

FIG. 7 also graphically illustrates initial and final blood glucose concentration observed in rats over two hours comparing a microemulsion preparation of the invention and a control based on the results of the in vivo experiments described in Example 2.

Figure 8:
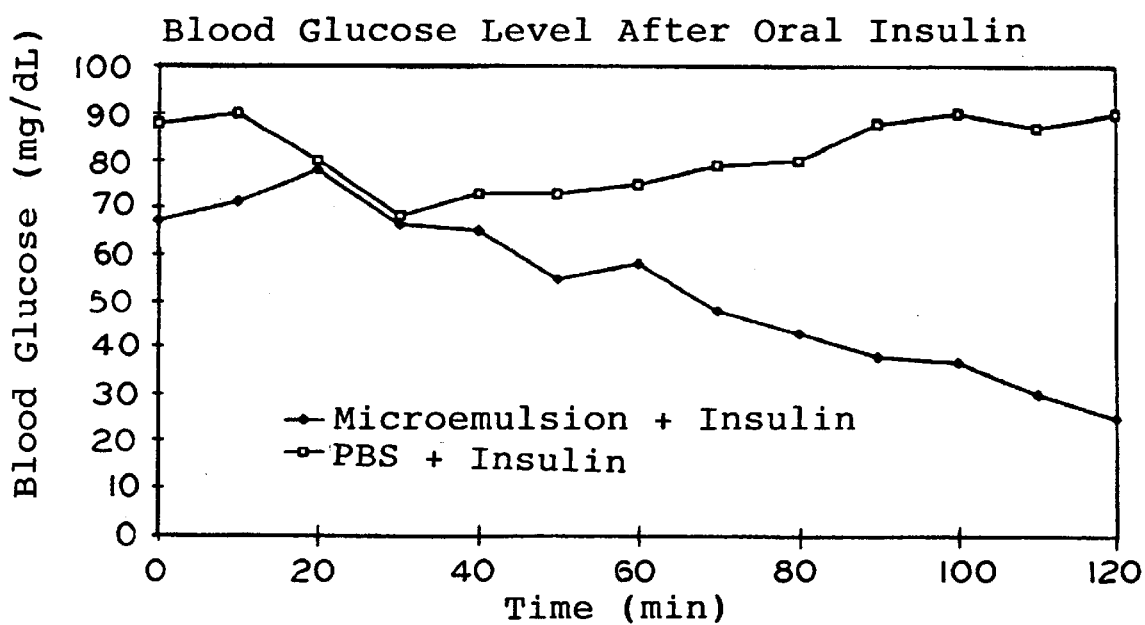

FIG. 8 graphically illustrates the control of blood glucose concentration after oral insulin administration observed in rats over two hours comparing a microemulsion preparation of the invention and a control based on the results of the in vivo experiments described in Example 2.

Figure 9:
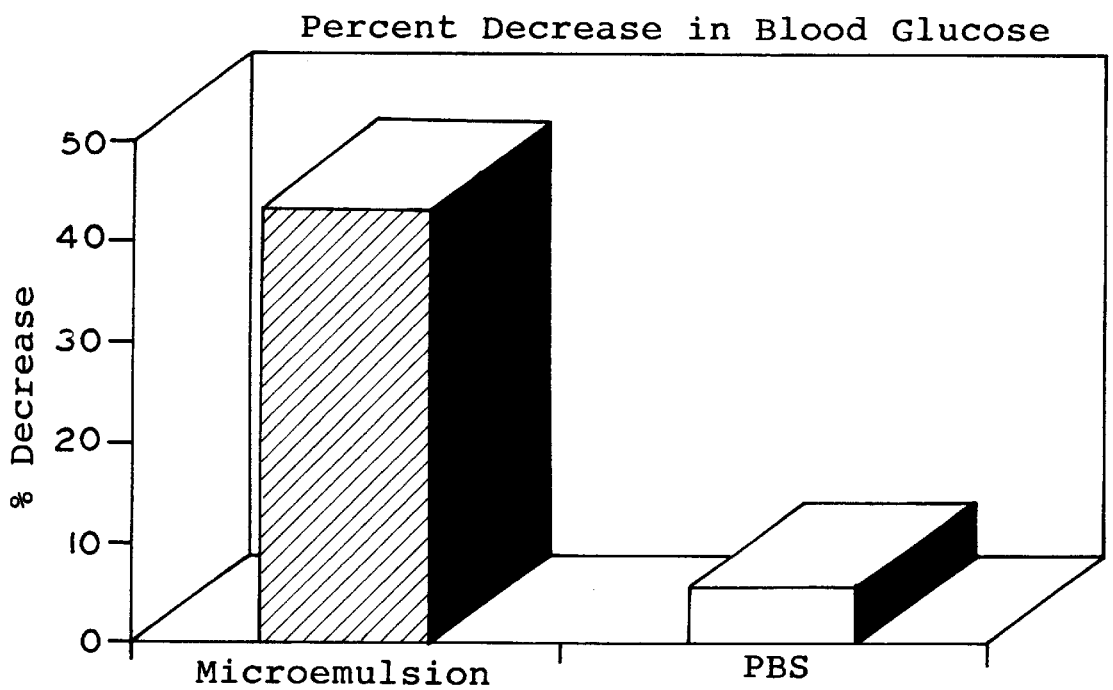

FIG. 9 graphically illustrates the percent decrease in blood glucose concentration after oral insulin administration observed in rats comparing a microemulsion preparation of the invention and a control based on the results of the in vivo experiments described in Example 2.

As used herein the term "insulin" refers to any of the various insulins that are known. Insulins are divided into three categories according to promptness, duration and intensity of action following subcutaneous administration, i.e., as mentioned above, rapid, intermediate or long-acting. Crystalline regular insulin is prepared by precipitation in the presence of zinc chloride and modified forms have been developed to alter the pattern of activity. Protamine zinc insulin (PZI) is the result of the reaction of insulin and zinc with the basic protein, protamine, to form a protein complex which dissolves and is absorbed more slowly than crystalline regular insulin but is highly reliable for absorption at a steady rate. Isophane is a modified crystalline protamine zinc insulin whose effects are comparable to a mixture of predominantly regular insulin with a lesser portion of protamine zinc insulin. The extended and prompt insulin-zinc suspensions are also contemplated for use in the invention. The insulin can be, for example, of human bovine, ovine or other animal origin or can be a recombinant product.

Human insulin is now widely available as a result of its production by recombinant DNA techniques; in theory it should be slightly less immunogenic than purified porcine insulin, which in turn should be less immunogenic than bovine insulin. Bovine insulin differs from human insulin by three amino acid residues, whereas porcine differs from human insulin by only one amino acid at the carboxyl-terminus of the B chain. However, when highly purified, all three insulins have a relatively low, but measurable, capacity to stimulate the immune response.

Short- or rapid-acting insulins are simply solutions of regular, crystalline zinc insulin (insulin injection) dissolved in a buffer at neutral pH. These have the most rapid onset of action but the shortest duration, i.e., glucose levels reach a low point within 20–30 minutes and return to baseline in about 2–3 hours.

Intermediate-acting insulins are formulated so that they dissolve more gradually when administered subcutaneously; their durations of action are thus longer. The two preparations most frequently used are neutral protamine Hagedorn (NPH) insulin (isophane insulin suspension) and Lente insulin (insulin zinc suspension). NPH insulin is a suspension of insulin in a complex with zinc and protamine in a phosphate buffer. Lente insulin is a mixture of crystallized (Ultralente) and amorphous (Semilente) insulins in an acetate buffer, which minimizes the solubility of insulin. The preparations have similar pharmacokinetic profiles.

Ultralente insulin (extended insulin zinc suspension) and protamine zinc insulin suspension are long-acting insulins; they have a very slow onset and a prolonged ("flat") peak of action. These insulins are advocated to provide a low basal concentration of insulin throughout the day.

As used herein the term insulin is also contemplated to encompass insulin analogs. Recent development of insulin that have altered rates of absorption have raised interest. Insulin with aspartate and glutamate substituted at positions B9 and B27, respectively, crystallizes poorly and has been termed "monomeric insulin". This insulin is absorbed more rapidly from subcutaneous depots and thus may be useful in meeting postprandial demands. By contrast, other insulin analogs tend to crystallize at the site of injection and are absorbed more slowly. Insulins with enhanced potency have been produced by substitution of aspartate for histidine at position B10 and by modification of the carboxyl-terminal residues of the B chain.

An emulsion is a dispersed system containing at least two immiscible liquid phases, a hydrophobic phase and a hydrophilic phase. The emulsion comprises the dispersed phase, the dispersion phase and an emulsifying agent or surfactant agent, except when the hydrophobic material is a "self-emulsifying" ester, whereby it is possible to produce an emulsion without a separate emulsifying agent. Usually one of the two immiscible liquids is an oil while the other is aqueous. Which phase becomes the dispersed phase depends on the relative amounts of the two liquid phases and which emulsifying agent is selected. Therefore, an emulsion in which the aqueous phase is dispersed as droplets throughout the hydrophobic phase is called an water-in-oil (w/o) emulsion and vice versa. The term "colloidal" refers to emulsions in which the dispersed phase is of very fine particles, usually less than about 1 mm in size. A "microcolloid" is an emulsion wherein the dispersed particles are usually about 100 um or less in size. Cosurfactants are also common components of microcolloids and are simply surfactants included in addition to the primary surfactant.

A "microemulsion" is an optically clear, isotropic and thermodynamically stable liquid. Microemulsions are composed of an oily phase, an aqueous phase, a surfactant and, sometimes, a cosurfactant. A homogeneous mixture forms when components of the microemulsion are mixed together in any order. The resulting composition is thermodynamically stable with either a water continuous phase, an oily continuous phase, or a bicontinuous combination of the phases. Specifically, the microemulsion of the invention is a water-in-oil microemulsion, with the oil as the continuous phase.

Microemulsions are ideal for oral insulin delivery systems since they are homogeneous, thermodynamically stable, have uniform droplet sizes of approximately 20–40 nanometers and are optically clear. A water-in-oil microemulsion, in particular, has small aqueous phase droplets, uniformly dispersed in a continuous oil phase. Therefore, the insulin is protected from proteolytic enzymes that are soluble in the digestive fluids. In general, the chemical structure of insulin dictates that it will be at least somewhat, if not mostly, water soluble, and thus will be located inside the water droplet or very near the surface of the droplet of the water-in-oil microemulsion system. Thus, the outer oily phase of the microemulsion prohibits migration of proteolytic enzymes through the delivery system. The outer oily phase of the microemulsion is also able to incorporate into the intestinal cell matrix, thus creating channels (either paracellularly or transcellularly) through which the insulin can pass. One general preparation procedure that maximizes insulin solubility is as follows: first, the insulin is prepared as a slurry in the aqueous phase at pH 2; second, the surfactant is added and mixed thoroughly; third, the oily phase is added and mixed to form the microemulsion. The ingredients of the microemulsion can be any of the below named surfactants, oily phases or aqueous phases.

In large-scale manufacture, these steps can be accomplished using standard mixing equipment employed in the production of ointments, creams and lotions. Specifically, mixing tanks made by Lee Industries (New Cumberland, Pa.) can be readily used. Regardless of the equipment employed, mixing needs to be accomplished using as low a shear rate as practical, in order to maintain the physical integrity of the insulin.

The incorporated peptide/protein is further protected from peptidases and proteases with the addition of a hydrophobic thickening agent in the oily phase. An additional hydrophobic ingredient, when added to the microemulsion, will form a thixotropic paste-like composition that will become liquified at 37° C., i.e., "body temperature".

Therefore, it is important to select a hydrophobic material that can erode or slowly dissolve in the intestine or become incorporated into the intestinal cell matrix so that the insulin is released. In addition, it is possible to combine the two approaches, for example, by incorporating enteric materials in the hydrophobic phase. This would preclude the necessity of coating the capsule with an enteric polymer.

In accordance with the present invention, certain hydrophobic materials provide enhanced absorption capabilities for oral delivery of insulin. These materials are selected from the group consisting of long chain carboxylic acids, long chain carboxylic acid esters, long chain carboxylic acid alcohols and mixtures thereof.

Further, certain materials, when combined in accordance with the invention to form a water-in-oil microemulsion, give enhanced absorption capabilities. These materials are an oily phase, composed of long chain carboxylic acids or esters of alcohols thereof, an aqueous phase composed primarily of water and a surface active agent, primarily of the non-ionic block copolymer type, that are mixed together to form a water-in-oil microemulsion.

The long chain carboxylic acids, generally contain 4–36 carbon atoms and preferably contain at least 12 carbon atoms, most preferably 12 to 22. In some cases this carbon chain is fully saturated and unbranched, while others contain one or more double bonds. They can have saturated, unsaturated, branched or straight chain hydrocarbon chains. A few contain 3-carbon rings or hydroxyl groups. The compounds are generally not surface active. They are poorly soluble in water and the longer the acid chain, the fewer the double bonds, the lower the solubility in water. The carboxylic acid group is polar and ionized at neutral pH. This accounts for the slight solubility of short-chain acids in water.

Examples of such acids are those ranging from $C_{16}$ to $C_{22}$ with up to three unsaturated bonds (also branching). Examples of saturated straight chain acids are n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid and melissic acid. Also useful are unsaturated monoolefinic straight chain monocarboxylic acids. Examples of these are oleic acid, gadoleic acid and erucic acid. Also useful are unsaturated (polyolefinic) straight chain monocarboxylic acids. Examples of these are linoleic acid, ricinoleic acid, linolenic acid, arachidonic acid and behenolic acid. Useful branched acids include, for example, diacetyl tartaric acid.

Examples of long chain carboxylic acid esters include, but are not limited to, those from the group of: glyceryl monostearates; glyceryl monopalmitates; mixtures of glyceryl monostearate and glyceryl monopalmitate (Myvaple 600, Eastman Fine Chemical Company); glyceryl monolinoleate; glyceryl monooleate; mixtures of glyceryl monopalmitate, glyceryl monostearate, glyceryl monooleate and glyceryl monolinoleate (Myverol 18-92, Eastman Fine Chemical Company); glyceryl monolinolenate; glyceryl monogadoleate; mixtures of glyceryl monopalmitate, glyceryl monostearate, glyceryl monooleate, glyceryl monolinoleate, glyceryl monolinolenate and glyceryl monogadoleate (Myverol 18-99, Eastman Fine Chemical Company); acetylated glycerides such as distilled acetylated monoglycerides (Myvacet 5-07, 7-07 and 9-45, Eastman Fine Chemical Company); mixtures of propylene glycol monoesters, distilled monoglycerides, sodium steroyl lactylate and silicon dioxide (Myvatex TL, Eastman Fine Chemical Company); d-alpha tocopherol polyethylene glycol 1000 succinate (Vitamin E TPGS, Eastman Fine Chemical Company); mixtures of mono- and di-glyceride esters such as Atmul (Humko Chemical Division of Witco Chemical); calcium stearoyl lactylate; ethoxylated mono- and di-glycerides; lactated mono- and di-glycerides; lactylate carboxylic acid ester of glycerol and propylene glycol; lactylic esters of long chain carboxylic acids; polyglycerol esters of long chain carboxylic acids, propylene glycol mono- and di-esters of long chain carboxylic acids; sodium stearoyl lactylate; sorbitan monostearate; sorbitan monooleate; other sorbitan esters of long chain carboxylic acids; succinylated monoglycerides; stearyl monoglyceryl citrate; stearyl heptanoate; cetyl esters of waxes; stearyl octanoate; $C_{10}$–$C_{30}$ cholesterol/lavosterol esters; and sucrose long chain carboxylic acid esters.

Examples of the self-emulsifying long chain carboxylic acid esters include those from the groups of stearates, pamitates, ricinoleates, oleates, behenates, ricinolenates, myristates, laurates, caprylates, and caproates.

The alcohols useful in the invention are exemplified by the hydroxyl forms of the carboxylic acids exemplified above and also strearyl alcohol.

Additives to the carboxylic acid/alcohol phase can be used to create a solid at room temperature. This addition affords the opportunity to make better use of enteric coatings. Examples of such additives are glycerol behenate, cetyl alcohol, stearic acid, sorbitan ester derivatives such as sorbitan stearate, sorbitan isostearate, polyethylene glycol 1000 to 6000, saturated polyglycolised glycerides, acrylic polymers, glyceryl monoricinoleate, palmitic acid, myristic acid, and polyvinyl acetate.

Such ingredients could be, but are not limited to, long chain carboxylic acids or esters or alcohols thereof which are paste or solid at room temperature, or which upon incorporation into the microemulsion form a gel, such as glyceryl behenate, cetyl alcohol, stearyl alcohol, stearic acid, sodium stearate, saturated polyglycolised glycerides, acrylic polymers, myverol 18-92, myverol 18-99, myvacet 9-45, vitamin E TPGS, vitamin E-6-100, glyceryl monoricinoleate, Gelucire 44-14, palmitic acid, myristic acid, polyvinyl acetate.

Such a paste formulation is incorporated into a convenient oral dosage form of the pharmaceutical agent. One such dosage form is to incorporate the microemulsion into a gelatin capsule. The gelatin capsule can be either hard shell or soft shell. The particular preference of the invention is the soft shell gelatin capsule. The convenient oral dosage form would allow ease of swallowing and may be coated with a polymer of the enteric coating type, such that the polymer is impervious to an acidic environment like that found in the stomach, but would dissolve in the relatively basic environment like that found in the intestine.

The types of protective or sustained release coatings that can be used include, but are not limited to, ethylcellulose, hydroxypropylmethylcellulose, hydroxypropylcellulose, hydroxyethylcellulose and esters of methacrylic and ethacrylic acid (Eudragit RL, RS, and NE polymer products, Rohm Pharma, Darmstadt, Germany). The enteric protective materials or coatings can be, for example, cellulose acetate pthalate, hydroxypropylmethylcellulose pthalate, ethylvinylacetate pthalate, polyvinylacetate pthalate and esters of methacrylic and ethacrylic acid (Eudragit S, Eudragit L and Eudragit E30D, Rohm Pharma, Darmstadt, Ger.).

The composition or preparation of the invention can further include a surfactant, or a mixture of two or more surfactants. A surfactant is an amphiphilic molecule consisting of a hydrophobic tail and a hydrophilic head. These molecules possess distinct regions of both hydrophilic and hydrophobic character. The hydrophobic tail can be a hydrocarbon or fluorocarbon chain of 8 to 18 carbon atoms. They are long chain molecules such as, for example, soaps or detergents. Surface active agents or surfactants are long chain molecules, such as soaps and detergents, which accumulate at the hydrophilic/hydrophobic(water/oil) interface and lower the surface tension at the interface. One effect of a reduced surface tension is the stabilization of the emulsions. This is because molecules with both polar and nonpolar groups become oriented such that the hydrocarbon tail embeds itself into the hydrophobic phase and the hydrophilic head protrudes into the hydrophilic phase. Where the hydrophobic composition or other component of the preparation includes a surface-active agent, such as a surfactant, it is usually present in amounts of about 0.05% to 50.0% weight/weight of the hydrophobic composition with a preferred range of 1.0% to 3.0% (w/w). Preferred surfactants include, for example, the Tween(polyoxyethylene sorbate) family of surfactants(ICI, Wilmington Del.), the Span (sorbitan long chain carboxylic acid esters) family of surfactants(ICI), the Pluronic(ethylene or propylene oxide block copolymers) family of surfactants (BASF, Parsippany N.J.), the Labrasol, Labrafil and Labrafac(each polyglycolyzed glycerides) families of surfactants(Gappe Fosse, St. Priest, France), sorbitan esters of oleate, stearate, laurate or other long chain carboxylic acids, poloxamers (polyethylene-polypropylene glycol block copolymers or the Pluronic® brand of surfactants, BASF, Parsippany, N.J.), other sorbitan or sucrose long chain carboxylic acid esters, mono and diglycerides, PEG derivatives of caprylic/capric triglycerides and mixtures thereof.

Microemulsions are generally formed by adding the aqueous phase, oily phase, and surfactant to a suitable vessel and mixing. If any of the ingredient is a solid, it should be added to a liquid phase in which it is soluble and heated to dissolve. For example, if the surfactant is a solid, and it is soluble in the oily phase, then it should be dissolved completely, then followed with aqueous phase, etc. On the other hand, if the surfactant is soluble in the aqueous phase, then it should first be added to the aqueous phase, dissolved completely, followed by the oily phase. Appropriate mixing devices as mentioned above can be employed for this purpose.

The preparation of an water-in-oil emulsion based system, requires that the insulin be dispered into the hydrophilic material as described above, with the hydrophobic phase being added in the presence of surfactant or self-emulsifying hydrophobic long chain carboxylic acid ester. This emulsion is then filled into a soft or hard gelatin capsule. The capsule may be further processed to provide gastric protection by enterically coating the capsule.

In accordance with the invention, insulin is incorporated into the microemulsions by admixture using conventional mixing devices and homogenizers used for semi-solid ointments and lotions, with agitation at speeds common to emulsified products such as creams and emulsions. Examples of common equipment employed are propeller or turbine mixers, homogenizers, colloid mills, ultrasonic mixers and microfluidizers. Examples of such brand name mixing equipment are Lee Kettle, Gaulin mixer and Stephan. The shear of the agitation should be sufficient to form a stable dispersion, but not too great to cause degradation of the insulin. The shear forces will form aggregates that have diameters ranging from 100–500 angstroms. Suitable homogenizers are available from Micromedics, Inc., Silverson, and APV Crepaco, Arde Barinco. Stephen and Fryma mixers can also be employed with suitable vacuum to prevent formation of bubbles. Monitoring and evaluation of pH, viscosity, specific gravity and aggregate sizes are necessary.

EXAMPLE 1

Transport of Insulin across Caco-2 cells Using an Insulin Microemulsion Formulation The following materials were used as received to prepare the insulin microemulsion: Pluronic L44 (BASF, Parsippany, N.J.), Linoleic acid (Everseol 221, Emery Group, Henkle, Cincinnati, Ohio), Hand buffer (Biofluids, Rockville, Md.). The microemulsion consists of 27.3% Pluronic L44, 63.6% Linoleic acid, and 9.95% Hanks buffer. The insulin was incorporated into the microemulsion as the microemulsion was in preparation as follows.

A stock solution of insulin was prepared by adding insulin to Hanks buffer at pH 2. The surfactant Pluronic L44 was then added and mixed thoroughly. The linoleic acid was added last. Table 1 gives the concentrations of insulin in the stock solutions, the final concentration of insulin in the microemulsion (referred to as microemulsion 34A) and the amount dosed to the Caco-2 cells and the rat intestine, in units insulin per gram microemulsion.

TABLE 1

Concentration of Insulin in the formulation of insulin microemulsion vehicles

| Membrane | Insulin/Hanks Stock units/ml | Insulin/Microemulsion units/g µE | Units Dosed |
|---|---|---|---|
| Caco-2 cells | 35.75 units/ml | 3.54 units/g µE | 5.67 units/ml* |
| Rat Intestine | 90.75 units/ml | 8.17 units/g µE | 8.17 units/ml* |

*Assume microemulsion with a density of 1.

The Caco-2 cell line has been established as the primary screening model for oral peptide delivery. Caco-2 cells are derived from a colon cancer and differentiate in culture to form intestinal epithelium similar to that found in the small intestine. The cells form a monolayer with many of the specific properties of the epithelial lining of the intestine: they form a brush border with normal enzymes, they form tight junctions between cells, and they acquire the barrier properties of an enterocyte sheet. When grown on permeable supports these cells can be used to screen drug microemulsion formulations.

Caco-2 colon carcinoma cells were obtained from American Type Culture Collection (Rockville, Md.) and maintained in culture in high glucose DMEM with 10% fetal calf serum, plus pen/strep, at 37° C., in 5% $CO_2$. Cells were subcultured roughly every 5–7 days, 1:3 in T75 flasks, or when cells were 80–90% confluent, as determined by visual inspection. Caco-2 cells are adherent and were disassociated from the surface of the flask by incubation at room temperature with 0.25% trypsin in Hanks balanced salt solution (HBSS) without calcium or magnesium. Caco-2 cells are contact inhibited and when they become confluent, begin to differentiate and lose the capacity to undergo mitosis. To maintain a consistent genotype, it is important to avoid selecting for a subset of cells that is not differentiated. This is done by subculturing working stocks of cells before they differentiate.

Transport experiments used 2.45 cm Transwell cell culture inserts with 3.0 µm pores (Costar, Boston, Mass.). These are plastic inserts for tissue culture wells, which allow a distinct apical and basal compartment only connected by small pores in the growing surface. Cells are seeded on the upper surface of the insert at $3\times10^5$ cells per well and media changed every day. Media was changed in the lower compartments by lifting insert with a sterile forceps. The upper compartment holds 1.5 ml. and the lower 2.6 ml. Tissue culture reagents were purchased from GIBCO-Life Technologies (Gaithersburg, Md.) and Biofluids (Rockville, Md.).

Transport studies used differentiated cells, which are cells that have acquired many of the characteristics of normal intestinal epithelium including a brush border and barrier properties. Initial experiments established the time course of differentiation (see below) and transport studies used cells that fell into the time frame, which these experiments established, of 21–28 days.

For transport determinations, insulin transport enhancers were added to HBSS plus calcium and magnesium. Transport media containing insulin was added to the upper compartment of the Transwell, where the test solution was in contact with the apical surface of the cells. Transport was measured by taking aliquots from the lower compartment, which was in contact with the basal surface of the cells.

Studies were performed in a six well tissue culture plate and Transwells were moved to a new well every twenty minutes giving determinations for two hours, or every thirty minutes, for a total of three hours. Aliquots were removed from each well and insulin levels determined by RIA and HPLC. Transport was calculated as percent transport per hour from top to bottom. Because in all experiments the amount of insulin in the upper compartment was large compared to the amount transported, no correction was made for loss of insulin in the upper compartment with time.

Initial transport experiments used $^{125}I$ labeled insulin, in these experiments there was no increase in transport (data not shown). We considered the possibility that the additional size of iodination prevented transport. A radioimmuno assay (RIA) measures unlabeled insulin and was used for subsequent transport assay analysis. Insulin levels were assayed with a commercial RIA kit (Incstar, Stillwater, Minn.). Briefly an antibody, raised against insulin, forms a complex with $^{125}I$ labeled insulin. This complex is then incubated with insulin standards or experimental samples; the unlabeled insulin competes with the $^{125}I$ labeled insulin for binding to the antibody; greater amounts of added insulin result in lower levels of bound $^{125}I$. A standard curve is established and used to determine insulin levels in experimental samples. Unlabeled insulin at concentrations of 0, 5, 10, 50, 100, and 200 ng/ml was used to set up the standard curve. Experimental samples were diluted to fit the standard curve.

An HPLC assay for insulin was developed in order to examine whether the insulin being transported through the Caco-2 cells and the rat intestine was broken down or digested, as well as to test the efficacy of the radioimmunoassay being used to analyze the transport studies. Insulin was separated on a reverse-phase C-8 or C-18 column using a gradient of 0.1% TFA in water to 01% TFA in acetonitrile at a flow of 1.0 ml/min. The absorbance at 280 nm was monitored. The standards used in the development of the assay were from Sigma (St. Louis, Mo.) and included Insulin, Insulin chain A, Insulin chain B, Insulin chain B fragment (22–30), and Insulin chain C. Insulin that had been trypsin digested was also used to check separation.

The results of insulin transport in the Caco-2 cells is summarized in Table 2.

TABLE 2

Tabular results of insulin transport through Caco-2 cells

| Ingredients | µU Insulin Transported |
|---|---|
| Hank's | 12 |
| Pluronic L44 solution | 12 |
| Microemulsion 34A | 149 |

When data are separated into first and second hour, shown in Table 3, it is clear that tranport increases with time. Linoleic acid, which is the oily phase in the microemulsion, acts on intracellular mechanisms to open pores in the tight junctions with a similar time course. The surfactant, besides forming the microemulsion, acts synergistically to increase cell membrane fluidity allowing large molecules to pass through the pores in tight junctions.

TABLE 3

Results of insulin transport through Caco-2 cells, for each of two hours.

| Vehicle | Insulin (µU/mL) |
|---|---|
| Hank's hr 1 | 2.25 |
| Hank's hr 2 | 2.46 |
| Hank's T | 4.71 |
| Plu µE hr 1 | 24.34 |
| Plu µE hr 2 | 89.16 |
| Plu µE T | 113.50 |

This study has been replicated with the same result.

EXAMPLE 2

Oral Delivery of Insulin Microemulsion Preparations to Rats

The goal here is the in vivo investigation of microemulsion vehicles for the oral delivery of insulin. This example describes the protocols that have been developed.

These experiments (outlined below) are an extension of the cell culture-based studies in the human adenocarcinoma cell line Caco-2 (Artursson et al., Biochem. Biophys. Res. Comm., 175:880–885, 1991; Conradi et al., Pharmaceutical Research, 10:1790–1792, 1933). Rats are an appropriate model for these studies since the absorption of drugs has been widely documented as comparable to humans in many cases (Conradi et al., Pharmaceutical Research 10:1790–1792, 1993; Butterworth and Pelling, Journal of Physiology 232:60P–61P, 1973; Fujioka, et al., Pharm. and Pharmacol. 43:465–470, 1991; Hashimoto, et al., Pharm. and Pharmacol. 83:798–801, 1994; Karls, et al., Pharm. Res., 8:1477–1481, 1991; and Papperheimer, et al., Pro. Sci., 91:1942–1945, 1994). The in situ studies confirm the intestinal absorption of the insulin under physiological conditions.

1. In Situ Studies

During the procedure, the animal is maintained at 37° C. by a heating pad and lamp. The intestine is exposed by a midline incision. A portion of the jejunum (10 cm) is isolated by tying (4-0 silk, 20 cm) at either end with care taken not to disrupt the omentum. Small openings are made with scissors at either end of the tissue on the outer side of the silk. One end is secured by gently tightening the 4-0 silk.

Prior to introduction of the insulin formulation, a blood sample was drawn from the vein that runs along side the intestine (time=0) and a section of the intestine was lavaged with phosphate-buffered saline (PBS), pH 6.5 (3 mL). Every ten minutes after introduction of the insulin formulation (1 mL, 8.8 units insulin/mL) into the small intestine, blood (50 microliters) was drawn to monitor the blood glucose level. At 20 minute intervals, blood (500 microliters) was drawn for insulin determination as well as the glucose determination. Blood glucose was immediately determined on whole blood by the One Touch II™ glucometer (Life Scan, Johnson & Johnson, Milpitas, Calif.). The remaining blood sample was centrifuged to separate the plasma. Red blood cells were resuspended in saline (100 microliters) and returned through the mesenteric vein to the animal. Plasma (200 microliters) was frozen on dry ice for analysis of insulin levels by radioimmunoassay (RIA) (INCSTAR Corporation, Stillwater, Minn.).

A second group of five animals received the insulin in phosphate buffered saline solution. Blood samples are taken at the same time points that were defined for the microemulsion. The transport of drug from these animals is a measure of the basal transport in the absence of the microemulsion. For each formulation, a group of five rats is used for a single formulation of microemulsion.

2. Sample Analysis

Plasma is analyzed for insulin levels by RIA or HPLC.

Rat plasma is diluted directly for RIA or extracted by a solid-phase extraction (C-18 SEP-COLUMN; Peninsula Lab) for HPLC.

An HPLC method with UV detection has been developed to determine the levels of insulin. Plasma is deproteinized by addition of trichloroacetic acid and neutralized prior to injection. Separation of insulin is done by HPLC with a C-18 reverse phase column with UV detection at 254 nm) in potassium phosphate buffer (pH 2.6) mixed with acetonitrile in a ratio of 97.5:2.5 (w:w). Calculation of the peak area ratio for the standards and sample is used to determine the concentration of the samples.

The following examples describe formulations that further illustrate the water-in-oil emulsions of the invention that are suitable for insulin delivery. All percentages presented are volume-to-volume (v/v).

EXAMPLE 3

| Ingredients | % |
|---|---|
| Lente Insulin | 3.2 |
| Poloxamer 124 | 26.2 |
| Linoleic acid | 61.1 |
| Aqueous phase | 9.6 |

The above ingredients are mixed well using one of the above mentioned mixing devices in a suitable container to form an optically clear solution.

EXAMPLE 4

| Ingredients | % |
|---|---|
| Ultralente Insulin | 3.5 |
| Poloxamer 124 | 18.3 |
| Oleyl alcohol | 73.2 |
| Aqueous phase | 4.9 |

The above ingredients are mixed well using one of the above mentioned mixing devices in a suitable container to form an optically clear solution.

EXAMPLE 5

| Ingredients | % |
|---|---|
| Insulin, human zinc | 3.2 |
| Poloxamer 124 | 26.2 |
| Oleic acid | 61.1 |
| Aqueous phase | 9.6 |

The above ingredients are mixed well using one of the above mentioned mixing devices in a suitable container to form an optically clear solution.

EXAMPLE 6

| Ingredients | % |
|---|---|
| Insulin, human recombinant | 3.1 |
| Poloxamer 124 | 25.8 |

-continued

| Ingredients | % |
|---|---|
| Linoleic acid | 60.3 |
| Aqueous phase | 9.5 |
| Behenic acid | 1.3 |

Behenic acid is melted in linoleic acid in a suitable container at 50°–80° C. This is cooled to 40° C., the remaining ingredients are added and the preparation is well mixed. This microemulsion is a solid at room temperature.

EXAMPLE 7

| Ingredients | % |
|---|---|
| Insulin, isophane | 3.2 |
| Poloxamer 105 | 26.2 |
| Linoleic acid | 61.1 |
| Aqueous phase | 9.6 |

The above ingredients are mixed well using one of the above mentioned appropriate mixing devices in a suitable container to form an optically clear solution.

EXAMPLE 8

| Ingredients | % |
|---|---|
| Insulin, regular purified pork | 5 |
| Tween 20 | 35.1 |
| Arlacel 186 | 35.1 |
| Oleyl alcohol | 24.8 |

EXAMPLE 9

| Ingredients | % |
|---|---|
| Insulin, monomeric | 4.3 |
| Pluronic L44 | 25.9 |
| Hank's buffer | 9.5 |
| Oleyl alcohol | 51.7 |
| Ethanol | 8.6 |

EXAMPLE 10

Tween 20/Span 20 microemulsions containing linoleic acid and insulin zinc, prompt can be prepared having, for example, the formulations shown in Table 4.

TABLE 4

| Ingredients | 10A(%) | 10B | 10C | 10D | 10E |
|---|---|---|---|---|---|
| Insulin zinc, prompt | 3.8 | 3.8 | 3.8 | 3.8 | 3.8 |
| Tween 20 | 36.7 | 41.1 | 25.2 | 27.8 | 45.6 |
| Span 20 | 7.2 | 4.6 | 2.8 | | |
| Linoleic Acid | 45.8 | 45.6 | 65.3 | 64.9 | 45.6 |
| Hank's buffer | 4.4 | 4.9 | 2.9 | 3.5 | 5.0 |

EXAMPLE 11

Tween 20/Span 20 microemulsions containing linoleic acid, oleic acid or oleyl alcohol, as the oil phase and insulin zinc, extended, can be prepared having, for example, the formulations shown in Table 5.

TABLE 5

| Ingredients | 11A (%) | 11B | 11C | 11D | 11E | 11F |
|---|---|---|---|---|---|---|
| Insulin zinc, extended | 3.8 | 3.8 | 3.8 | 3.8 | 3.8 | 3.8 |
| Tween 20 | 36.7 | 41.1 | 25.2 | 27.8 | 45.6 | 37.4 |
| Span 20 | 9.2 | 4.6 | 2.8 | | | 9.3 |
| Oleic Acid | 45.8 | 45.6 | 65.3 | 64.9 | 45.6 | |
| Oleyl Alcohol | | | | | | 46.9 |
| Hank's buffer | 4.4 | 4.9 | 2.9 | 3.5 | 5.0 | 2.5 |

EXAMPLE 12

Further formulations with Tween 20 provide a microemulsion in which Span 20 is the cosurfactant. Span 20, or sorbitan monolaurate, acts as an ideal cosurfactant. Hank's buffer is the aqueous phase and linoleic acid, oleic acid or oleyl alcohol are preferred oil phases. Also, the Labrasol and Labrafac family of surfactants are saturated polyglycolised glycerides. An example of a microemulsion containing the surfactant Labrasol has Labrafac CM10 as the ideal cosurfactant. Examples using linoleic acid are shown in Table 6.

TABLE 6

| Ingredients | 12A (%) | 12B |
|---|---|---|
| Insulin, Ultralents Purified Beef | 4.9 | 4.9 |
| LAvrasol 36.2 | | |
| Labrafac CM10 | 9.0 | |
| Tween 20 | | 40.7 |
| Span 20 | | 4.5 |
| Linoleic Acid | 45.3 | 45.3 |
| Hank's buffer | 4.5 | 4.5 |

EXAMPLE 13

Formulations for Pluronic L44/oil phase/Hank's buffer microemulsions containing different fatty acids or alcohols as the oil phase and partial substitution of Hank's buffer with ethanol are exemplified in Table 7.

TABLE 7

| Ingredients | 13A (%) | 13B | 13C | 13D | 13E | 13F |
|---|---|---|---|---|---|---|
| Isophane Insulin | 4.3 | 4.3 | 4.3 | 4.3 | 4.3 | 4.3 |
| Pluronic L44 | 25.8 | 25.8 | 25.8 | 26.2 | 26.6 | 27 |
| Hank Buffer | 9.5 | 9.5 | 9.5 | 8.4 | 9.9 | 4.95 |
| Oleyl alcohol | 60.4 | | | | | |
| Oleic acid | | 60.4 | | | | |
| Linoleic acid | | | 60.4 | | | 60.4 |
| Linolenic acid | | | | | 60.7 | |
| Ricinoleic acid | | | | 61.1 | | |
| Ethanol | | | | | | 4.75 |

EXAMPLE 14

Formulations for Pluronic L44/fatty alcohol or acid/Hank's buffer containing oleyl alcohol, oleic acid or linoleic acid as the oil phase are exemplified in Table 8.

TABLE 8

| Formulation | Pluronic L44 | Oleyl Alcohol | Linoleic Acid | Oleic Acid | Hank's Buffer |
|---|---|---|---|---|---|
| 14A (%) | 27 | 63.1 | | | 9.9 |
| 14B | 28.3 | 66 | | | 5.7 |
| 14C | 41.8 | 41.8 | | | 16.3 |
| 14D | 44.76 | 44.76 | | | 10.47 |
| 14E | 47.44 | 47.44 | | | 5.12 |
| 14F | 19 | 75.9 | | | 5.1 |
| 14G | 34.2 | 51.3 | | | 9.4 |
| 14H | 27 | | | 63.1 | 9.9 |
| 14I (%) | 27 | | 63.1 | | 9.9 |
| 14J | 25.8 | | | 60.1 | 14.1 |
| 14K | 25.8 | | 60.1 | | 14.1 |
| 14L | 27 | | 63.1 | | 9.9 |
| 14M | 27 | | | 63.1 | 9.9 |
| 14N | 27 | | 63.1 | | 9.9 |
| 14O | 27 | | | 64.1 | 9.9 |
| 14P | 27 | | 63.1 | | 9.9 |
| 14Q | 26.8 | | 62.6 | | 9.8 |
| 14R | 25.5 | | 59.6 | | 15 |

All entries are percent-by-weight. Formulations A–F illustrate microemulsions having varying ratios of Pluronic L44/oleyl alcohol/Hank's buffer. Formulations H–K illustrate microemulsions having a Pluronic L44-to-oil phase ratio of 3:7 in which the oil phase is either oleic acid or linoleic acid and the percent of aqueous phase (Hank's buffer) varies from about 10% to about 14%. Formulations L and M illustrate microemulsions of Pluronic L44 with either linoleic acid or oleic acid, respectively, at a pH elevated to 6.5 using NaOH pellets. Formulations N and 0 were prepared at three different pH's (3.5, 4.5–5.0 and 6.0–6.5). Formulations P, Q and R were prepared at pH 3.5–3.8, 4.9 and 7, respectively. Each of the above formulations can be used to provide an insulin pharmaceutical preparation suitable for oral delivery, using any of the various types of insulins mentioned herein. The above formulations can be combined with insulin preparations (1 to 100 U insulin/mg formulation concentration) in ratios ranging from 100:1 to 5:1 (w:w).

EXAMPLE 15

Formulations for Pluronic L44/fatty alcohol or acid/Hank's buffer containing oleyl alcohol, oleic acid or linoleic acid with a substitution of ethanol for part of the Hank's buffer, a total substitution of Hank's buffer with ethanol and/or a change in the ratio of Pluronic L44 to linoleic acid to 2:8 are exemplified in Table 9.

TABLE 9

| Ingredients | 15A (%) | 15B | 15C | 15D | 15E |
|---|---|---|---|---|---|
| Pluronic L44 | 27 | 27 | 27 | 19 | 27.03 |
| Hank's buffer | 4.95 | 4.95 | | 5.1 | 9.91 |
| Oleyl alcohol | 63.1 | | | 75.9 | 54.04 |
| Oleic acid | | 63.1 | | | |
| Linoleic acid | | | 63.1 | | |
| Ethanol | 4.95 | 4.95 | 9.9 | | 9.01 |

Each of the above formulations can be used to provide an insulin pharmaceutical preparation suitable for oral delivery, using any of the various types of insulins mentioned herein. The above formulations can be combined with insulin preparations (1 to 100 U insulin/mg formulation concentration) in ratios ranging from 100:1 to 5:1 (w:w).

EXAMPLE 16

Formulations of Pluronic L44/linoleic acid/Hank's buffer with varying substitutions of ethanol and Pluronic L44/oleyl alcohol/Bank's buffer with ethanol substitutions.

TABLE 10

| Formulations | Pluronic L44 | Linoleic Acid | Ethanol | Hank's Buffer |
|---|---|---|---|---|
| 16A (%) | 27 | 63.1 | | 9.9 |
| 16B | 27 | 63.1 | 4.95 | 4.95 |
| 16C | 27 | 54.1 | 9 | 9.9 |
| 16D | 27 | 58.6 | 4.5 | 9.9 |
| 16E | 27 | 49.6 | 13.5 | 9.9 |
| 16F | 27 | 45.1 | 18.02 | 9.9 |
| 16G | 27 | 40.54 | 22.52 | 9.9 |
| 16H | 27 | 36 | 27 | 9.9 |
| 16I | 27 | 31.5 | 31.5 | 9.9 |
| 16J | 27 | 27 | 36 | 9.9 |

Each of the above formulations can be used to provide an insulin pharmaceutical preparation suitable for oral delivery, using any of the various types of insulins mentioned herein. The above formulations can be combined with insulin preparations (1 to 100 U insulin/mg formulation concentration) in ratios ranging from 100:1 to 5:1 (w:w).

EXAMPLE 17

This example illustrates the addition of water soluble surfactants sodium lauryl sulfate (SLS), sodium cholate and Tween 20 and the addition of an oil soluble additive, Eastman SAIB, to the microemulsion formulations, as shown in Table 11.

TABLE 11

| Ingredients | 17A (%) | 17B | 17C | 17D |
|---|---|---|---|---|
| Pluronic L44 | 27 | 27 | 27 | 27 |
| Hank's buffer | 9.9 | 9.9 | 9.9 | 9.9 |
| Linoleic acid | 63 | 63 | 63 | 63 |
| SLS | 0.1 | | | |
| Sodium cholate | | 0.1 | | |
| Tween 20 | | | 0.1 | |
| Eastman SAIB | | | | 0.111 |

Each of the above formulations can be used to provide an insulin pharmaceutical preparation suitable for oral delivery, using any of the various types of insulins mentioned herein. The above formulations can be combined with insulin preparations (1 to 100 U insulin/mg formulation concentration) at in ratios ranging from 100:1 to 5:1 (w:w).

EXAMPLE 18

This example illustrates the substitution of Pluronic L44 with Pluronic L62 or the combination of L64 and L35 in the microemulsion formulations, as shown in Table 12.

TABLE 12

| Ingredient | 18A | 18B | 18C |
|---|---|---|---|
| Pluronic L62 | 42.87 | | |
| Pluronic L64 | | 27 | |
| Hank's buffer | 14.4 | 9.9 | 9.9 |
| Linoleic acid | 42.8 | 63.1 | 63.1 |
| Pluronic L35 | | | 27 |

Each of the above formulations can be used to provide an insulin pharmaceutical preparation suitable for oral delivery, using any of the various types of insulins mentioned herein. The above formulations can be combined with insulin preparations (1 to 100 U insulin/mg formulation concentration) in ratios ranging from 100:1 to 5:1 (w:w).

EXAMPLE 19

This example illustrates the inclusion of a fatty ester material in the Pluronic L44 or Tween 20/Span 20 microemulsions. All of the materials are GRAS or food grade.

TABLE 13

| Ingredient | 19A (%) | 19B | 19C | 19D | 19E |
|---|---|---|---|---|---|
| Myverol 18-99 | 0.9 | 0.95 | | | |
| Myvacet 9-45 | | | 0.9 | 0.95 | |
| Tenox GT-2 | | | | | 0.9 |
| Linoleic Acid | 61.8 | 46.7 | 61.8 | 46.7 | 61.8 |
| Aqueous | 11.8 | 4.7 | 11.8 | 4.7 | 11.8 |
| Tween 20 | | 42.9 | | 42.9 | |
| Span 20 | | 4.75 | | 4.75 | |
| Pluronic L44 | 25.5 | | 25.5 | | 25.5 |

| Ingredient | 19F (%) | 19G | 19H | 19I | 19J |
|---|---|---|---|---|---|
| Tenox GT-2 | | 0.95 | | | |
| Vitamin E 6-100 | | 0.90 | 0.95 | | |
| Vitamin E TPGS | | | | 8.6 | |
| Myverol 18-99 | | | | | 9.5 |
| Linoleic Acid | 46.7 | 63.1 | 46.7 | 48.6 | 46.6 |
| Aqueous | 4.7 | 9.9 | 4.7 | 18.4 | 4.7 |
| Tween 20 | 42.9 | | 42.9 | | 34.3 |
| Span 20 | 4.75 | | 4.75 | | 4.8 |
| Pluronic L44 | | 26.1 | 24.5 | | |

TABLE 14

| Ingredient | 19B (%) | 19C | 19D | 19F |
|---|---|---|---|---|
| Myverol 18-92 | 0.95 | | | |
| Glycerolmonoricinoleate | 0.90 | 0.95 | 9.5 | |
| Pluronic L44 | | 25.6 | | |
| Tween 20 | 42.9 | | 42.9 | 34.3 |
| Span 20 | 4.76 | | 4.76 | 4.76 |
| Linoleic Acid | 46.7 | 61.7 | 46.7 | 46.7 |
| Aqueous | 4.7 | 11.8 | 4.7 | 4.74 |

Each of the above formulations can be used to provide an insulin pharmaceutical preparation suitable for oral delivery, using any of the various types of insulin mentioned herein. The above formulations can be combined with insulin preparation 1 to 100 Units insulin/mg formulation concentration) in ratios ranging from 100:1 to 5:1 (w:w).

What is claimed is:

1. A pharmaceutical composition comprising:
   (a) a water-in-oil emulsion comprising:
      (i) a continuous hydrophobic phase comprising at least one member selected from the group consisting of oleic acid, gadoleic acid, erucic acid, linoleic acid, linolenic acid, ricinoleic acid, arachidonic acid, glyceryl esters of such acids, oleyl alcohol and d-alpha-tocopherol polyethylene glycol succinate;
      (ii) a discontinuous aqueous hydrophilic phase;
      (iii) at least one surfactant for dispersing said hydrophilic phase in said hydrophobic phase as a water-in-oil emulsion, wherein said at least one surfactant includes a member selected from the group consisting of poloxamer 124, a polyglycolized glyceride, sorbitan laurate and polyoxyethylene (20) sorbitan monooleate; and
   (b) insulin in said aqueous hydrophilic phase.

2. The composition of claim 1 wherein the hydrophobic phase includes linoleic acid.

3. The composition of claim 1 wherein the hydrophobic phase includes linoleic acid and oleyl alcohol.

4. The composition of claim 1 wherein the hydrophobic phase includes glyceryl behenate in combination with a member selected from the group consisting of oleyl alcohol, oleic acid, glyceryl monooleate, linoleic acid, linolenic acid, ricinoleic acid and mixtures thereof.

5. The composition of claim 1 wherein the hydrophobic phase includes d-alpha tocopherol polyethylene glycol succinate.

6. The composition of claim 1 wherein the hydrophobic phase includes at least one of linoleic acid and linolenic acid and further includes at least one of d-alpha tocopherol polyethylene glycol succinate or sucrose acetate isobutyrate.

7. The composition of claim 1 wherein at least one of the surfactants includes poloxomer 124.

8. The composition of claim 1 wherein at least one of the surfactants includes a polyglycolized glyceride.

9. The composition of claim 1 wherein at least one of the surfactants includes polyoxyethylene sorbitan monooleate.

10. The composition of claim 1 wherein the surfactant includes polyoxyethylene (20) sorbitan monooleate and sorbitan laurate.

11. The composition of claim 1 wherein the aqueous hydrophilic phase is present in an amount of about 5.1 to about 9.9 weight percent of the emulsion.

12. The composition of claim 1 wherein the aqueous hydrophilic phase includes a water soluble alcohol.

13. The composition of claim 1 wherein the aqueous hydrophilic phase includes a balanced saline solution.

14. The composition of claim 1 wherein the surfactant is present in a range of from about 19 to about 27 weight percent of the emulsion.

15. The composition of claim 1 wherein the hydrophobic phase is present in a range of about 63.1 to about 75.9 weight percent of the emulsion.

16. The composition of claim 1 wherein the emulsion is encapsulated in a capsule comprising an enteric coating material.

17. The composition of claim 1 wherein the enteric coating material is soluble in an acidic aqueous environment.

18. The composition of claim 1 wherein the ester of the hydrophobic phase is a monoglyceryl ester.

* * * * *

UNITED STATES PATENT AND TRADEMARK OFFICE
CERTIFICATE OF CORRECTION

PATENT NO. : 5,824,638
DATED : October 20, 1998
INVENTOR(S) : Beth A. Burnside, et al.

It is certified that error appears in the above-identified patent and that said Letters Patent is hereby corrected as shown below:

On the title page:

Item: [73] Assignee: Shire Laboratories, Inc., Gaithersburg, Md.

Signed and Sealed this

Twentieth Day of April, 1999

Attest:

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO. : 5,824,638

DATED : October 20, 1998

INVENTOR(S) : Burnside, et al.

It is certified that error appears in the above-identified patent and that said Letters Patent is hereby corrected as shown below:

On the title page, items [75] and [73] should read:

item [75] Inventors: Beth A. Burnside, Silver Springs, Md.; Carol E. Mattes, Pittsburgh, Pa.; Charlotte M. McGuinness, Bethesda, Md.; Edward M. Rudnic, North Potomac, Md.; George W. Belendiuk, deceased, late of Potomac, all of Md. by Krystyna Belendiuk, Executrix item [73] Assignee: Shire Laboratories Inc., Rockville, Md.

Signed and Sealed this

Thirty-first Day of August, 1999

Attest:

Q. TODD DICKINSON

*Attesting Officer*  *Acting Commissioner of Patents and Trademarks*